United States Patent [19]

Bernstein et al.

[11] 4,209,614
[45] Jun. 24, 1980

[54] VITAMIN $B_{12}$ DERIVATIVE SUITABLE FOR RADIOLABELING

[75] Inventors: Jack Bernstein, New Brunswick; Ravi K. Varma, Belle Mead, both of N.J.; B. Richard Vogt, Yardley, Pa.; Frank L. Weisenborn, Titusville, N.J.

[73] Assignee: E. R. Squibb & Sons, Inc., Princeton, N.J.

[21] Appl. No.: 910,568

[22] Filed: May 30, 1978

[51] Int. Cl.² .................. A61K 31/68; C07H 23/00
[52] U.S. Cl. .................. 536/25; 23/230 R; 424/1.5; 424/12
[58] Field of Search .......................................... 536/25

[56] References Cited
U.S. PATENT DOCUMENTS

| | | | |
|---|---|---|---|
| 3,459,855 | 8/1969 | Thuillier | 536/25 |
| 3,981,863 | 9/1976 | Niswender et al. | 536/25 |

OTHER PUBLICATIONS

Kim et al. "Jour. Nucl. Med.", vol. 17, No. 8, 1976, pp. 737–739.

Endres et al. "Clin. Chem.", vol. 24, No. 3, 1978, pp. 460–465.

Primary Examiner—Johnnie R. Brown
Attorney, Agent, or Firm—Lawrence S. Levinson; Donald J. Barrack

[57] ABSTRACT

Radiolabeled vitamin $B_{12}$ derivatives having the formula

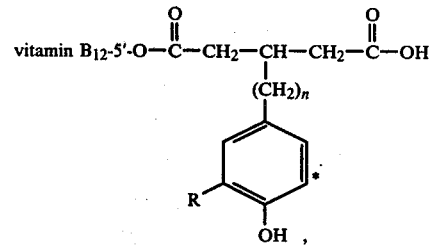

wherein R is hydrogen or alkyl of 1 to 3 carbon atoms; n is 0, 1, 2, 3 or 4; and the asterisk (*) indicates tagging with a radioisotope, are useful as tracers in radioassays.

11 Claims, No Drawings

VITAMIN B₁₂ DERIVATIVE SUITABLE FOR RADIOLABELING

BACKGROUND OF THE INVENTION

Vitamin B$_{12}$ radioassays are known in the art. For the most part, these radioassays have been based on competitive protein binding utilizing vitamin B$_{12}$ binding protein isolated from sources such as human serum and hog intrinsic factor. Recently, a radioimmunoassay for the determination of vitamin B$_{12}$ levels in sample fluids has been disclosed. Endres, Paiter and Niswender, "A Solid-Phase Radioimmunoassay for Vitamin B$_{12}$ in Serum, With Use of Radioiodinated Tyrosine Methyl Ester of Vitamin B$_{12}$", *Clin. Chem.*, 24(3):460-465 (1978), disclose the preparation of the tyrosine methyl ester of vitamin B$_{12}$ and its radioiodination for use as a radioactive tracer. An analogous, but broadened, disclosure of vitamin B$_{12}$ derivatives which can be radioiodinated for use in a radioimmunoassay procedure can be found in United States patent 3,981,863, issued Sept. 21, 1976 to Niswender and Hudson.

BRIEF DESCRIPTION OF THE INVENTION

Vitamin B$_{12}$ derivatives having the formula

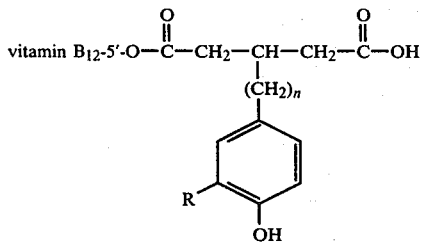

are readily tagged with a radioisotope and can be used (when radiolabeled) as a tracer in radioassay procedures for the determination of Vitamin B$_{12}$ levels in a body fluid. In formula I, and throughout the specification, R is hydrogen or an alkyl group of 1 to 3 carbon atoms and n is 0, 1, 2, 3 or 4.

DETAILED DESCRIPTION OF THE INVENTION

The vitamin B$_{12}$ derivatives of formula I are prepared from vitamin B$_{12}$ and a glutaric anhydride derivative having the formula

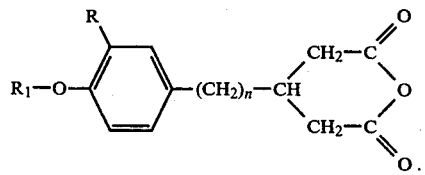

In formula II, and throughout the specification, R$_1$ is an alkanoyl group having 2 to 6 carbon atoms, acetyl being the preferred group.

The anhydrides of formula II are disclosed in copending United States patent applications Serial Nos. 901,952, filed May 1, 1978 now abandoned and Ser. No. 908,294 filed May 22, 1978. They can be prepared by first reacting a 4-methoxyphenyl aldehyde having the formula

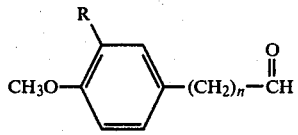

with at least 2 molar equivalents of cyanoacetic acid in the presence of a base (e.g., sodium hydroxide) to yield, on acid hydrolysis, a compound having the formula

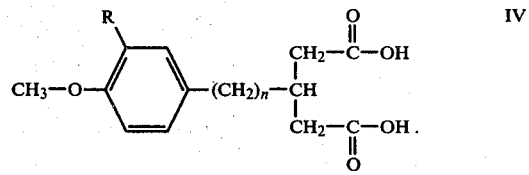

An alternative preparation for the compound of formula IV wherein n is O and R is hydrogen, i.e., 3-(4-methoxyphenyl)glutaric acid, is disclosed by Smith et al., J.A.C.S., 72, 1877 (1950). In that procedure, anisaldehyde is condensed with ethyl acetoacetate in the presence of piperidine to give ethyl anisal-bisacetoacetate. Clevage of this product to give the desired 3-(4-methoxyphenyl)glutaric acid can be accomplished with boiling alcoholic sodium hydroxide solution.

Demethylation of the glutaric acid derivatives of formula IV results in glutaric acid derivatives having the formula

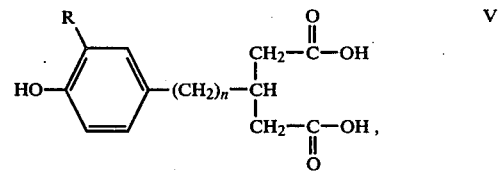

and can be accomplished by following one of the several procedures known in the art for the demethylation of aryl methyl ethers. One such procedure, described by Feutrill et al., *Aust. J. Chem.*, 25, 1719 (1972), involves the treatment of the aryl methyl ether with thioethoxide ion (readily prepared in situ from ethanethiol and sodium hydride) in a polar aprotic solvent, preferably dimethylformamide.

The phenolic hydroxy group of a compound of formula V can be protected with an alkanoyl group using art-recognized procedures. One such procedure comprises reacting the glutaric acid derivative with the appropriate acid anhydride (acetic anhydride is preferred). The preferred method of preparing a glutaric anhydride derivative of formula II from the glutaric acid derivative of formula V is to combine the conversion of the acid to anhydride and the protection of the phenolic hydroxy group into a single step. When the R$_1$ protecting group is acetyl, this would involve heating a glutaric acid derivative of formula V in acetic anhydride.

The reaction of vitamin B$_{12}$ and a glutaric anhydride derivative of formula II yields a compound having the formula

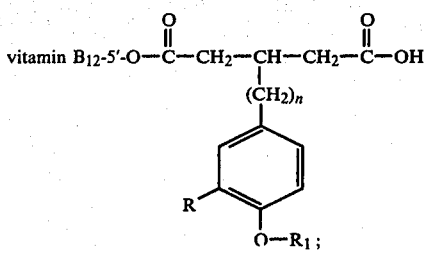

the reaction can be run in the presence of an organic base. Exemplary organic bases are nitrogen containing heterocyclics, e.g., pyridine, and tertiary amines, e.g., triethylamine. The reaction will preferably be run at an elevated temperature.

Removal of the phenolic hydroxyl protecting group in a compound of formula VI yields the corresponding product of formula I.

The compounds of formula I can be coupled with an immunogenic carrier, such as a high molecular weight protein of which bovine serum albumin and thyroglobulin are exemplary, and if necessary an adjuvant in order to produce a substance capable of inducing antibody formation in animals. Procedures for such couplings are well known in the art; see, for example, Parker, "Radioimmunoassay of Biologically Active Compounds", Prentice-Hall, Inc., New Jersey (1976).

The compounds of formula I can be labeled ("tagged") with a radioisotope, preferably iodine-125 or iodine-131, and most preferably iodine-125, using procedures well known in the art, to yield a radiolabeled compound having the formula

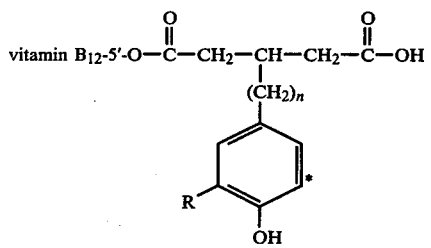

The asterisk (*) in formula VII indicates tagging with a radioisotope. Exemplary of the methods known in the art is the method of Hunter and Greenwood; see *Nature*, 194:495 (1962). The radiolabeled compounds of formula VII form an integral part of this invention.

The vitamin $B_{12}$ radiolabeled compounds of this invention can be used as tracers in conventional radioassays following procedures well known in the art, using hog intrinsic factor as the binding protein. Additionally, the vitamin $B_{12}$ radiolabeled compounds of this invention can be used as tracers in radioimmunoassays following the general principles known in the art; see, for example, Parker et al., "Radioimmunoassay of Biologically Active Compounds," Prentice Hall, Inc. New Jersey (1976) or Endres, Painter, and Niswender, "A Solid-Phase Radioimmunoassay for Vitamin $B_{12}$ in Serum, With Use of Radioiodinated Tyrosine Methyl Ester of Vitamin $B_{12}$", *Clin. Chem.*, 24(3):460–465 (1978). The carboxyl group on the radiolabeled compounds of this invention allows for the separation of radiolabeled tracer bound to the binding protein from unbound (free) radiolabeled tracer using ion exchange separation techniques. This feature helps make the radiolabeled compounds of this invention useful in the automated radioimmunoassay system disclosed by Brooker et al, United States Pat. No. 4,022,577.

The following examples are specific embodiments of this invention.

EXAMPLE 1

5′-O-[3-(4-Hydroxyphenyl)glutaroyl]vitamin $B_{12}$

(A) 3-(4-Methoxyphenyl)glutaric acid

A mixture of p-anisaldehyde (27.2 g), ethyl acetoacetate (52.1 g) and piperidine (4 ml) in 95% ethanol (10 ml) is stirred at room temperature for 5.0 hours while a solid forms. The solid is isolated by filtration, washed with 25% ethanol and crystallized from 95% ethanol to afford ethyl 2,2′-(4-methoxybenzal)-bis-acetoacetate (31.4 g), melting point 138°–141° C. The filtrate on dilution with an equal amount of water gives a solid which is crystallized from 95% ethanol to afford another crop of material (8.5 g), melting point 137°–142° C.

A mixture of ethyl 2,2′-(4-methoxybenzal)-bis-acetoacetate (30 g), ethanol (450 ml) and 50% sodium hydroxide (450 g) is refluxed vigorously for 1.0 hour. Water (150 ml) is added and most of the ethanol is removed by distillation in vacuo. The concentrate is acidified with concentrated hydrochloric acid and is extracted with ethyl acetate. The ethyl acetate solution is washed with brine, dried, evaporated, and the residue is crystallized from benzenemethanol to afford 3.3 g of 3-(4-methoxyphenyl)glutaric acid, melting point 147°–150° C.

(B) 3-(4-Hydroxyphenyl)glutaric acid

To a stirred suspension of 57% sodium hydrideparaffin (6.45 g), in dry dimethylformamide (70 ml) is slowly added ethanethiol (11.89 ml) in dry dimethylformamide (20 ml). After stirring the resultant slurry for 15 minutes, a solution of 3-(4-methoxyphenyl)glutaric acid (3.0 g) in dry dimethylformamide (20 ml) is added. The slurry is heated in a bath at 165°to C. for 5.0 hours and most of the solvent is removed by distillation in vacuo. The residue is diluted with water, acidified with concentrated hydrochloric acid and extracted twice with ether (the extracts are discarded). The solution is saturated with sodium chloride and extracted with ethyl acetate. The ethyl acetate solution is washed once with brine, dried, and the residue crystallized from chloroform-hexane to afford 2.3g of 3-(4-hydroxyphenyl)glutaric acid, melting point 168–170° C.

(C) 3-[(4-Acetyloxy)phenyl]glutaric anhydride

A solution of 3-(4-hydroxphenyl)glutaric acid (800 mg) in acetic anhydride (15 ml) is heated at 100° C. for 2.5 hours and evaporated to dryness in vacuo. The residual solid is crystallized from chloroform-hexane to afford 600 mg of 3-(4-acetyloxyphenyl)-glutaric anhydride, melting point 140–143° C.

(D) 5′-O-[3-[4-(Acetyloxy)phenyl]glutaroyl]vitamin $B_{12}$

Vitamin $B_{12}$, 0.1012g, is dissolved in methanol and precipitated by the addition of ethyl acetate and toluene. Removal of the solvents and drying of the residue in vacuo at 50° C. for 30 minutes gives 100.1mg of amorphous solid. To this solid is added, under a nitrogen atmosphere, 201mg of 3-[(4-acetyloxy)phenyl]-glutaric anhydride (recrystallized from ethyl acetate, melting point 153–155° C.), 3 ml of dimethylsulfoxide and 0.5 ml of pyridine (both the dimethylsulfoxide and pyridine are dried with type 4A molcular sieves). The resulting solution is left at room temperature in the dark for 48 hours and 116.4mg of crude product is then precipitated by the addition of ethyl acetate.

The crude product is chromatographed on a 2.5×48 cm column of Whatman DE52 cellulose (acetate), eluting at 4ml/minute with a linear gradient prepared from 2 liters of 0.1M pyridine and 2 liters of 0.2M pyridinium acetate. The effluent is monitored at 360nm and 20ml fractions are collected. Unreacted vitamin $B_{12}$ is eluted in fractions 10 and 11, monglutarate in fractions 45 to 54 and diglutarate (trace) fractions 76 to 100. Fractions 51 to 54 comprise a weak shoulder. Fractions 45 to 50 are combined and taken to dryness in vacuo. The residue is precipitated from methanol with ethyl acetate, yielding 79.1mg of 5'-O-[3-[4-(Acetyloxy)phenyl]glutaroyl]-vitamin $B_{12}$.

(E) 5'-O-[3-(4-Hydroxyphenyl)glutaroyl]vitamin $B_{12}$

5'-O-[3-[4-(Acetyloxy)phenyl]glutaroyl]-vitamin $B_{12}$ (64.9mg) is dissolved in 65ml of water and 0.65ml of saturated aqueous sodium bicarbonate. The resulting solution, pH 8.8, is heated at 50° C. in the dark for 4 hours; the progress of the reaction is monitored by high pressure liquid chromatography. The solution is cooled to room temperature, adjusted to pH 2.0 with hydrochloric acid and applied to a 10 ml column of reverse phase adsorbent, 100 to 200 mesh macroreticular unfunctionalized divinylbenzene-cross-linked polystyrene. After washing the column with 100 ml of water, the product is eluted with methanol. The eluate is concentrated in vacuo and the residue, 67mg, is chromatographed on a 2.5×46 cm column of DEAE-cellulose (acetate form), eluting at 4ml/minute with a linear gradient prepared from 2 liters of 0.1M pyridine and 2 liters of 0.1M pyridinium acetate. The effluent is monitored at 550nm and 20ml fractions are collected. The curve obtained shows that the product, fractions 72 to 98, is not homogeneous. Fractions 72 to 98 are combined, concentrated in vacuo, and the residue is precipitated from methanol with ethyl acetate. The resulting solid is dissolved in water and lyophilized, yielding 60.1mg of crude 5'-O-[3-(4-hydroxyphenyl)-glutaroyl]vitamin $B_{12}$.

EXAMPLES 2–6

Following the procedure described in Example 1D, but substituting the anhydride reagent listed in column I for 3-[(4-acetyloxy)phenyl]glutaric anhydride, yields the vitamin $B_{12}$ derivative listed in column II.

| | Column I | Column II |
|---|---|---|
| 2. | 3-[4-(acetyloxy)-3-methyl-phenyl]glutaric anhydride | 5'-0-[3-(4-hydroxy-3-methylphenyl)glutaroyl]-vitamin $B_{12}$ |
| 3. | 3-[[4-(acetyloxy)phenyl]-methyl]glutaric anhydride | 5'-0-[3-[(4-hydroxyphenyl)methyl]glutaroyl]vitamin $B_{12}$ |
| 4. | 3-[2-[4-(acetyloxy)phenyl]-ethyl]glutaric anhydride | 5'-0-[3-[2-(4-hydroxyphenyl)ethyl]glutaroyl]vitamin $B_{12}$ |
| 5. | 3-[3-[4-(acetyloxy)phenyl]-propyl]glutaric anhydride | 5'-0-[3-[3-(4-hydroxyphenyl)propyl]glutaroyl]vitamin $B_{12}$ |
| 6. | 3-[4-[4-(acetyloxy)phenyl]-butyl]glutaric anhydride | 5'-0-[3-[4-(4-hydroxyphenyl)butyl]glutaroyl]vitamin $B_{12}$ |

DETAILED PROCEDURE FOR RADIOIODINATION OF VITAMIN $B_{12}$ DERIVATIVE

Method 1

To an aqeuous solution of 5'-O-[3-(4-hydroxyphenyl)-glutaroyl] vitamin $B_{12}$(20 μl; 500 μg/ml) in a glass vial is added 40 μm of 0.5M phosphate buffer, pH 7.4. Sodium radioiodide ($I^{125}$) aqueous solution (5 μl; 520 μCi/μl) is added to the vial and the vial is stoppered. Freshly diluted chloramine-T solution (20 μl; 0.5 μg/ml) in phosphate buffer (0.5M, pH 7.4) is injected into the vial and the vial is mixed for about 30 seconds and then allowed to stand for an additional 30 seconds. Sodium metabisulfite solution (20 μl; 0.5 μg/μl in 0.5M phosphate buffer, pH 7.4) is injected through the stopper to quench the reaction. The vial is mixed well. The iodination mixture is purified using thin layer chromatography.

Method 2

To an aqueous solution of 5'-O-[3-(4-hydroxyphenyl)-glutaroyl] vitamin $B_{12}$ (20 μl; 500 μg/ml) in a glass vial is added 40 μl of 0.5M phosphate buffer, pH 7.4. Sodium radioiodide ($I^{125}$) aqueous solution (10 μl; 520 μCi/μl) is added to the vial and the vial is stoppered. Freshly diluted chloramine-T solution (20 μl; 2 mg/μl) in phosphate buffer (.5M, pH 7.4) is injected into the vial and the vial is mixed for about 30 seconds and then allowed to stand for an additional 4.5 minutes. Sodium metabisulfite solution (20 μl; 2 μg/μl in 0.5M phosphate buffer, pH 7.4) is injected through the stopper to quench the reaction. The vial is mixed well. The iodination mixture is purified using thin layer chromatography.

What is claimed is:

1. A vitamin $B_{12}$ derivative having the formula

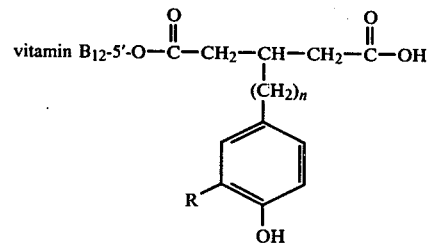

wherein R is hydrogen or an alkyl group of 1 to 3 carbon atoms and n is 0, 1, 2, 3 or 4.

2. A vitamin $B_{12}$ derivative in accordance with claim 1 wherein n is 0.

3. A vitamin $B_{12}$ derivative in accordance with claim 1 wherein n is 1.

4. A vitamin $B_{12}$ derivative in accordance with claim 1 wherein n is 2.

5. A vitamin $B_{12}$ derivative in accordance with claim 1 wherein n is 3.

6. A vitamin $B_{12}$ derivative in accordance with claim 1 wherein n is 4.

7. A vitamin $B_{12}$ derivative in accordance with claim 1 wherein R is hydrogen.

8. A vitamin $B_{12}$ derivative in accordance with claim 1 wherein R is an alkyl group of 1 to 3 carbon atoms.

9. A vitamin $B_{12}$ derivative in accordance with claim 1 having the name 5'-O-[3-(4-hydroxyphenyl)-glutaroyl]vitamin $B_{12}$.

10. A radiolabeled vitamin $B_{12}$ derivative having the formula

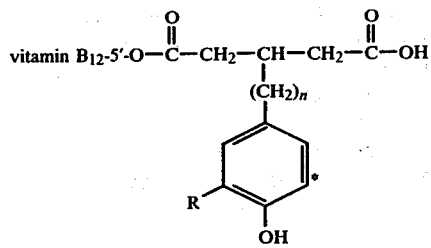

wherein R is hydrogen or alkyl of 1 to 3 carbon atoms; n is 0, 1, 2, 3, or 4; and the asterisk (*) indictes tagging with iodine-125 or iodine-131.

11. A radiolabeled vitamin $B_{12}$ derivative in accordance with claim 10 wherein the radioisotope is iodine-125.